United States Patent [19]

Eckersley

[11] 4,225,523
[45] Sep. 30, 1980

[54] ANTHRAQUINONE DYESTUFFS

[75] Inventor: Dennis Eckersley, Manchester, England

[73] Assignee: Imperial Chemical Industries Limited, London, England

[21] Appl. No.: 64,527

[22] Filed: Aug. 7, 1979

[30] Foreign Application Priority Data

Oct. 9, 1978 [GB] United Kingdom ............... 39812/78

[51] Int. Cl.$^2$ .......................................... C07C 143/665
[52] U.S. Cl. ...................................... 260/371; 260/373
[58] Field of Search ......................... 260/371, 373, 377

[56] References Cited

U.S. PATENT DOCUMENTS

| | | | |
|---|---|---|---|
| 2,195,067 | 3/1940 | Weinand et al. | 260/371 |
| 2,730,534 | 1/1956 | Hoefle et al. | 260/371 |
| 3,202,550 | 8/1965 | Grossmann et al. | 204/35 N |

FOREIGN PATENT DOCUMENTS 1250943  9/1967  Fed. Rep. of Germany .
1502684  3/1978  United Kingdom .

*Primary Examiner*—Winston A. Douglas
*Assistant Examiner*—Raymond K. Covington
*Attorney, Agent, or Firm*—Cushman, Darby & Cushman

[57] ABSTRACT

Anthraquinone dyestuffs which in the free acid form are of the formula:

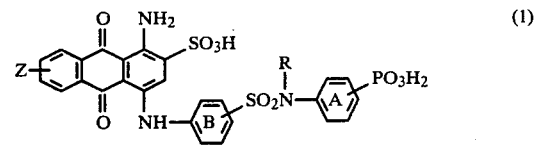

where
  Z is H or $SO_3H$,
  R is H, $C_{1-4}$alkyl or hydroxy $C_{1-4}$alkyl, the ring A may optionally be additionally substituted by $OCH_3$ and/or $SO_3H$.

These dyes are especially valuable for application to cellulose and fixation by heating with a carbodiimide such as dicyandiamide.

9 Claims, No Drawings

ANTHRAQUINONE DYESTUFFS

This invention relates to anthraquinone dyestuffs in particular to anthraquinone dyestuffs having a phosphonic acid group.

Several dyestuffs of the anthraquinone series having phosphonic acid groups are known. For example, see Swiss Pat. No. 394,422, U.S. Pat. No. 3,202,550 German Auslegeschrift No. 1250943, French Pat. No. 7504134 and U.K. Pat. No. 1502684. The present invention relates to a novel class of such dyesuffs which usually have a desirable bright shade and are associated with a good level of light fastness which is usually better than that of the known dyes.

According to the present invention there are provided anthraquinone dyestuffs which in the free acid form are of the formula:

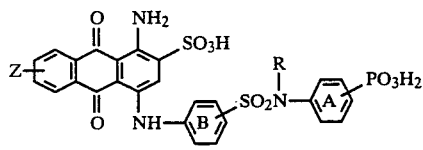

where
Z is H or $SO_3H$,
R is H, $C_{1-4}$alkyl or hydroxy $C_{1-4}$alkyl,
the ring A may optionally be additionally substituted by $OCH_3$ and/or $SO_3H$.

Preferred dyestuffs of formula (1) are those having one or more of the following features:
(a) Z is H
(b) R is H
(c) the ring A has no additional substituents
(d) the

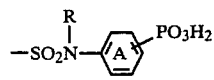

group on ring B is in the para or especially meta position, and (e) the $—PO_3H_2$ group on ring A is in the para or especially meta position.

Thus a particularly preferred dyestuff is of the formula:

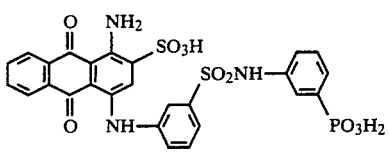

The present invention further provides a process for the manufacture of the dyestuffs of formula (1) which comprises reacting an anthraquinone sulphon chloride of the formula:

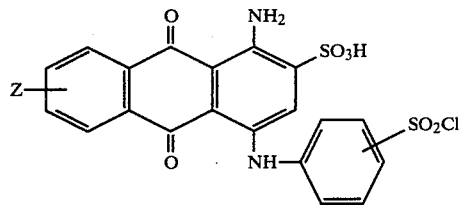

with an aminophenylphosphonic acid of the formula:

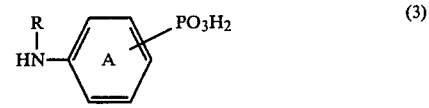

where Z and R have the meanings given above and the ring A may optionally have additional substituents as given above.

This process is conveniently carried out in an aqueous medium at 0° to 20° C. by additions of an acid-binding agent such as sodium carbonate, bicarbonate or hydroxide.

The anthraquinone sulphon chloride of formula (2) may be obtained by reacting bromoanthraquinone compounds of the formula:

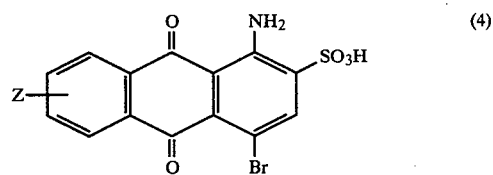

where Z has the meaning given above, with an aniline sulphonic acid, e.g. metanilic or sulphanilic acid and converting the sulphonic acid group into its sulphon chloride.

As examples of the aminophenyl phosphonic acids of formula (3) there may be mentioned:
3- and 4-aminophenyl phosphonic acid
N-methyl-3- and 4-aminophenyl phosphonic acid
N-(2-hydroxyethyl)-3- and 4-aminophenyl phosphonic acid
4-methoxyl-3-aminophenyl phosphonic acid 2-amino-4-phosphonobenzene sulphonic acid
2-methoxy-3-amino-5-phosphonobenzene sulphonic acid The present invention provides an alternative process for the manufacture of dyestuffs of formula (1) in which R is other than H, which comprises reacting a bromoanthraquinone compound of formula (4) with an amino compound of the formula:

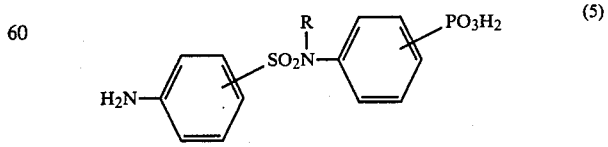

where R is $C_{1-4}$alkyl or hydroxy $C_{1-4}$alkyl.

This reaction is conveniently conducted in aqueous medium at 50° to 100° C. in the presence of an acid binder e.g. sodium carbonate or sodium bicarbonate and a copper catalyst e.g. cuprous chloride.

The amino compounds of formula (5) can be obtained by reacting compounds of the formula:

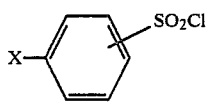 (6)

with aminophenyl phosphonic acids of formula (3) as given above, the symbol X representing a group inert during this reaction but which is subsequently converted to an amino group. Typically X is an acetylamino group which is converted to amino by hydrolysis or nitro which is converted to amino by reduction. The compounds of formula (6) are obtained from sulphonic acids

such 3-nitrobenzene sulphonic acid or 4-acetylaminobenzene sulphonic acid by conventional means, e.g. reaction with chlorosulphonic acid.

The alternative process for the manufacture of dyestuffs of formula (1) is usually found less convenient than the first process described above.

The dyestuff may be isolated from the above processes by conventional methods in the acid form or in the form of an amonium salt or partly in one of these forms and partly as an alkali metal, e.g. Li, Na or K salt. These salts can be obtained by adding a halide, e.g. the chloride of the desired alkali metal or ammonium halide, or ammonia to the completed reaction mixture before isolation. Alternatively, addition of an alkanolamine, e.g. diethanolamine, to the completed reaction mixture, a highly soluble form of the dyestuff is obtained which can be used as a total liquor for the dyeing or printing process.

The new dyestuffs are soluble in water owing to the presence of sulphonic and phosphonic acid groups. They can be used, in general, for the colouration of textile materials which can be dyed by dyes solubilised by anionic groups, e.g. natural and synthetic polyamide materials, e.g. wool, silk, polyhexamethylene adipamide and polycaproimide, but more especially natural or regenerated cellulose textile materials, e.g. cotton, linen and viscose rayon; in the case of cellulose textile materials, they are preferably fixed on the fibre by baking at a temperature of from 95° to 230° C. in the presence of a carbodiimide, e.g. cyanamide, dicyandiamide, e.g. by the method described in U.K. Pat. No. 1411306.

Textiles coloured by dyes of the present invention have strong bright shades and show good fastness to washing treatments. They are also often associated with good light fastness and in this respect they are usually superior to known anthraquinone dyes having phosphonic acid groups.

The dyes of the present invention are particularly suitable for application together with disperse dyestuffs from a single dyebath or print paste and in this respect compare favourably with, for example, most conventional cellulose reactive dyes which require the presence of alkaline adjuncts that frequently lead to flocculation of the disperse dyestuff. Such mixed dyebaths or print pastes are frequently desirable when colouring textile materials containing two types of fibre, e.g. cellulose and polyester blends.

The invention is illustrated by the following examples in which parts are by weight:

EXAMPLE 1

A stirred suspension of 20.52 parts of 1-amino-4-(3'-chlorosulphonylanilino)anthraquinone-2-sulphonic acid (prepared by the method of Example 1 of U.K. Pat. No. 952497) in 100 parts of ice-water, is added over 1 hour at 0°–5° C. to a stirred neutral solution of 8.65 parts of 3-aminophenyl phosphonic acid in 100 parts of water. The reaction mixture is maintained throughout the addition and for a subsequent 2 hours at 0°–5° C. and at pH 6.5–7.5 by the gradual addition of sodium hydroxide solution. The mixture is then stirred overnight at room temperature. The product is precipitated by the addition of concentrated hydrochloric acid (36°Tw.), the precipitated dyestuff is filtered, washed with 2 N hydrochloric acid and is finally sucked dry. The filtercake is dissolved in water by the addition of ammonia liquor to give a solution of pH 7.0. The solution is dialysed through a Visking membrane until free of halide. The dye solution is evaporated to dryness in vacuo.

EXAMPLES 2–4

In place of the 8.65 parts of 3-aminophenyl phosphonic acid used in Example 1 there may be used an equivalent amount of:

Example 2-4-aminophenyl phosphonic acid

Example 3-3-amino-4-methoxyphenyl phosphonic acid

Example 4-2-aminophenyl phosphonic acid when dyes are obtained which give bright reddish-blue shades on cellulose textile materials with excellent fastness to light and washing when applied by the process described in U.K. No. 1411306.

EXAMPLES 5–6

In place of the 20.52 parts of 1-amino-4-(3'-chlorosulphonylanilino)anthraquinone-2-sulphonic acid used in Example 1, there may be used an equivalent amount of:

Example 5

1-amino-4-(4'-chlorosulphonylanilino)anthraquinone-2-sulphonic acid (prepared by the method of example 2 of U.K. Pat. No. 952497).

Example 6

1-amino-4(2'-chlorosulphonylanilino)anthraquinone-2-sulphonic acid when dyes are obtained which give bright reddish-blue shades on cellulose textile materials with excellent fastness to light and washing when applied by the process described in U.K. No. 1411306.

What we claim is:

1. An anthraquinone dyestuff which in the free acid form is of the formula:

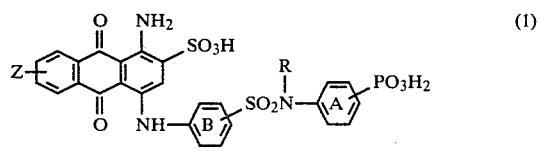 (1)

where

Z is H or $SO_3H$,

R is H, $C_{1-4}$alkyl or hydroxy $C_{1-4}$alkyl, the ring A may optionally be additionally substituted by OCH$_3$ and/or SO$_3$H.

2. A dyestuff as claimed in claim 1 in which Z is H.

3. A dyestuff as claimed in claim 1 in which R is H.

4. A dyestuff as claimed in claim 1 in which the ring A has no additional substituents.

5. A dyestuff as claimed in claim 1 in which the

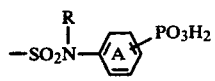

group on the ring B is in the meta or para position.

6. A dyestuff as claimed in claim 5 in which the

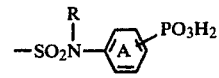

group is in the meta position.

7. A dyestuff as claimed in claim 1 in which the PO$_3$H$_2$ group is on ring A in the meta or para position.

8. A dyestuff as claimed in claim 7 in which the PO$_3$H$_2$ group is on ring A in the meta position.

9. A dyestuff as claimed in claim 1 of the formula:

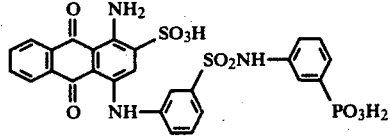

* * * * *